(12) United States Patent
Joshi et al.

(10) Patent No.: US 10,399,102 B2
(45) Date of Patent: Sep. 3, 2019

(54) SPILL-RESISTANT FLUID DELIVERY DEVICE

(71) Applicant: Microlin, LLC, Salt Lake City, UT (US)

(72) Inventors: Ashok V. Joshi, Salt Lake City, UT (US); John H Gordon, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 0 days.

(21) Appl. No.: 15/485,206

(22) Filed: Apr. 11, 2017

(65) Prior Publication Data

US 2017/0274399 A1    Sep. 28, 2017

Related U.S. Application Data

(63) Continuation-in-part of application No. 15/396,759, filed on Jan. 2, 2017, which is a continuation-in-part
(Continued)

(51) Int. Cl.
*A61M 5/145* (2006.01)
*B05B 11/00* (2006.01)
(Continued)

(52) U.S. Cl.
CPC .......... *B05B 11/0059* (2013.01); *A61L 9/122* (2013.01); *A61L 9/127* (2013.01);
(Continued)

(58) Field of Classification Search
CPC ............ A61M 5/1483; A61M 5/14593; A61M 5/155; A61M 2005/14204; B67D 7/72; F16N 11/10; B05B 11/0059
(Continued)

(56) References Cited

U.S. PATENT DOCUMENTS 3,471,349 A    10/1969    Cohen
3,504,827 A    4/1970    Larson
(Continued)

OTHER PUBLICATIONS

Ahn, Yae Y, Written Opinion of the International Searching Authority, PCT Application No. PCT/US2003/056662 (corresponding to U.S. Appl. No. 14/010,242 (dated Nov. 25, 2013), 1-8.
(Continued)

*Primary Examiner* — Alexander M Valvis
(74) *Attorney, Agent, or Firm* — Brian C. Trask

(57) ABSTRACT

An orientation independent delivery device. The delivery device includes a gas chamber, a delivery chamber, a gas cell, and a delivery aperture. The gas chamber includes a gas-side rigid portion and a gas-side flexible barrier. The gas-side flexible barrier is sealed to the gas-side rigid portion. The delivery chamber includes a delivery-side rigid portion and a delivery-side flexible barrier. The delivery-side flexible barrier is sealed to the delivery-side rigid portion and is oriented adjacent to the gas-side flexible barrier. The gas cell is coupled to the gas-side rigid portion of the gas chamber. The gas cell increases a gas pressure within the gas chamber to expand the gas-side flexible barrier. Expansion of the gas-side flexible barrier applies a compressive force to the delivery-side flexible barrier allowing a delivery material to escape from the delivery chamber.

18 Claims, 11 Drawing Sheets

Figure 1:
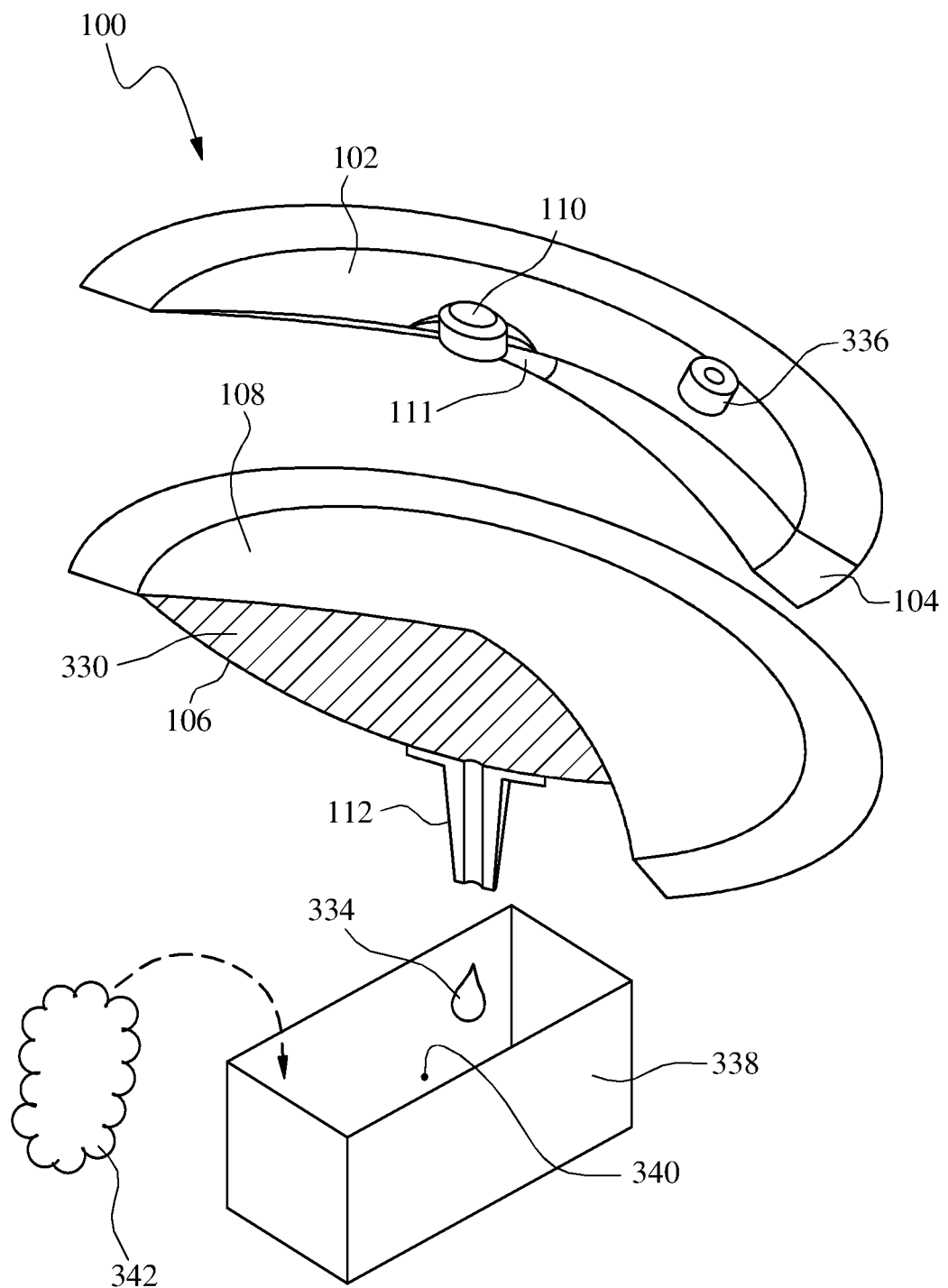

Related U.S. Application Data of application No. 14/632,970, filed on Feb. 26, 2015, now Pat. No. 9,533,066, and a continuation-in-part of application No. 14/537,691, filed on Nov. 10, 2014, now Pat. No. 9,623,135, application No. 15/485,206, which is a continuation-in-part of application No. 14/010,242, filed on Aug. 26, 2013, now Pat. No. 9,840,361.

(60) Provisional application No. 61/944,698, filed on Feb. 26, 2014, provisional application No. 61/692,750, filed on Aug. 24, 2012, provisional application No. 61/902,031, filed on Nov. 8, 2013.

(51) Int. Cl.

| | | |
|---|---|---|
| *A61M 5/20* | (2006.01) | |
| *B05B 11/04* | (2006.01) | |
| *C25B 9/06* | (2006.01) | |
| *C25B 1/04* | (2006.01) | |
| *A61M 5/148* | (2006.01) | |
| *A61M 5/155* | (2006.01) | |
| *B05B 9/047* | (2006.01) | |
| *B05B 11/02* | (2006.01) | |
| *C25B 1/12* | (2006.01) | |
| *C25B 5/00* | (2006.01) | |
| *C25B 9/00* | (2006.01) | |
| *A61L 9/12* | (2006.01) | |
| *A61M 5/142* | (2006.01) | |

(52) U.S. Cl.
CPC ...... *A61M 5/1483* (2013.01); *A61M 5/14593* (2013.01); *A61M 5/155* (2013.01); *A61M 5/2046* (2013.01); *B05B 9/047* (2013.01); *B05B 11/00412* (2018.08); *B05B 11/02* (2013.01); *B05B 11/046* (2013.01); *B05B 11/3028* (2013.01); *C25B 1/04* (2013.01); *C25B 1/12* (2013.01); *C25B 5/00* (2013.01); *C25B 9/00* (2013.01); *C25B 9/06* (2013.01); *A61L 2209/134* (2013.01); *A61M 2005/14204* (2013.01); *A61M 2205/19* (2013.01); *A61M 2205/8218* (2013.01); *Y02E 60/366* (2013.01)

(58) Field of Classification Search
USPC ................ 222/108, 318; 239/17, 20, 23, 54, 239/124–127
See application file for complete search history.

(56) References Cited

U.S. PATENT DOCUMENTS

| | | | |
|---|---|---|---|
| 3,940,032 | A | 2/1976 | Gershon |
| 3,945,539 | A | 3/1976 | Sassong |
| 4,358,026 | A | 11/1982 | Makinen |
| 5,090,963 | A | 2/1992 | Gross et al. |
| 5,398,851 | A * | 3/1995 | Sancoff ............ A61M 5/14593 222/386.5 |
| 5,399,166 | A | 3/1995 | Laing |
| 5,573,646 | A | 11/1996 | Saito et al. |
| 5,700,245 | A * | 12/1997 | Sancoff ............ A61M 5/14593 222/399 |
| 5,738,657 | A | 4/1998 | Bryant |
| 5,744,014 | A | 4/1998 | Gordon et al. |
| 5,891,097 | A * | 4/1999 | Saito ................... A61M 5/1483 604/131 |
| 5,899,381 | A | 5/1999 | Gordon et al. |
| 7,681,809 | B2 * | 3/2010 | Maget ................. A01M 1/2044 222/187 |
| 2009/0078724 | A1* | 3/2009 | Lamb .................... B60P 3/0257 222/608 |
| 2012/0060947 | A1 | 3/2012 | Reichert |
| 2013/0095225 | A1 | 4/2013 | LeBaron |

OTHER PUBLICATIONS

Extended European Search report, PCT Application No. PCT/US2003/056662 (corresponding to U.S. Appl. No. 14/010,242, dated Mar. 31, 2016.

* cited by examiner

SPILL-RESISTANT FLUID DELIVERY DEVICE

RELATED APPLICATIONS

This application is a continuation-in-part of U.S. Utility patent application Ser. No. 14/010,242, filed Aug. 26, 2013 and titled "GAS CELL DRIVEN ORIENTATION INDEPENDENT DELIVERY DEVICE", which claims the benefit of the filing date of U.S. Provisional Application Ser. No. 61/692,750, filed Aug. 24, 2012; and is a continuation-in-part of U.S. Utility patent application Ser. No. 15/396,759, filed Jan. 2, 2017 and titled "NO-DRIP VOLATILE SUBSTANCE DELIVERY SYSTEM", which is a continuation-in-part of U.S. Utility patent application Ser. No. 14/632,970, filed on Feb. 26, 2015, now U.S. Pat. No. 9,533,066, issued Jan. 3, 2017 and titled "VOLATILE SUBSTANCE DELIVERY SYSTEM, which claims the benefit of the filing date of U.S. Provisional Application Ser. No. 61/944,698, filed on Feb. 26, 2014, and is a continuation-in-part of U.S. Utility patent application Ser. No. 14/537,691, filed Nov. 10, 2014 and titled "VOLATILE SUBSTANCE DELIVERY SYSTEM", which claims the benefit of the filing date of U.S. Provisional Application Ser. No. 61/902,031, filed on Nov. 8, 2013, the disclosures of all of which are hereby incorporated in their entirety by this reference as though set forth herein.

BACKGROUND

Field of the Invention:

This invention relates to pumps and devices configured to dispense controlled amounts of fluid. It is particularly directed to spill-resistant fluid delivery systems.

Background:

Liquid and gas delivery systems serve many roles in many different fields from medical treatment devices to air fresheners. Frequently, conventional delivery systems involve some variety of a pump. Many different types of pumps exist with different strengths and weaknesses.

For example, some pumps are orientation sensitive. These pumps must be aligned or situated within certain thresholds to function properly. Other pumps require large amounts of operating force to move small amounts of material. Some pumps are susceptible to debris and particulate matter within a fluid stream.

SUMMARY

Embodiments of a device are described. In one embodiment, the device is an orientation independent delivery device. The delivery device includes a gas chamber, a delivery chamber, a gas cell, and a delivery aperture. The gas chamber includes a gas-side rigid portion and a gas-side flexible barrier. The gas-side flexible barrier is sealed to the gas-side rigid portion. The delivery chamber includes a delivery-side rigid portion and a delivery-side flexible barrier. The delivery-side flexible barrier is sealed to the delivery-side rigid portion. The delivery-side flexible barrier is oriented adjacent to the gas-side flexible barrier. The gas cell is coupled to the gas-side rigid portion of the gas chamber. The gas cell increases a gas pressure within the gas chamber to expand the gas-side flexible barrier. Expansion of the gas-side flexible barrier applies a compressive force to the delivery-side flexible barrier. The delivery aperture allows a delivery material to escape from the delivery chamber in response to compression of the delivery-side flexible barrier into the delivery chamber. Other embodiments of the device are also described.

Embodiments of a method are also described. In one embodiment, the method is a method for manufacturing a delivery device. The method includes forming a gas-side rigid portion, forming a gas-side flexible barrier, sealing the gas-side rigid portion to the gas-side flexible barrier to form a gas chamber, forming a delivery-side rigid portion, forming a delivery-side flexible barrier, sealing the delivery-side rigid portion to the delivery-side flexible barrier to form a delivery chamber, sealing the gas chamber to the delivery chamber with the gas-side flexible barrier oriented adjacent to the delivery-side flexible barrier. The method also includes disposing a gas cell in the gas-side rigid portion. The gas cell is in communication with the gas chamber. The method also includes, disposing a delivery aperture in the delivery-side rigid portion. The delivery aperture is in communication with the delivery chamber. Other embodiments of the method are also described Embodiments of a system are also described. In one embodiment, the apparatus is a delivery system. The system includes a delivery pump, a dispersion structure, and a control module. The delivery pump operates independent of orientation. The delivery pump includes a gas chamber, a gas cell, and a delivery chamber. The gas chamber includes a gas-side flexible barrier and a gas-side rigid portion. The gas cell is disposed in communication with the gas chamber to increase pressure within the gas chamber and distend the gas-side flexible barrier away from the gas-side rigid portion by generating a gas within the gas chamber. The delivery chamber includes a delivery-side flexible barrier and a delivery-side rigid portion. The delivery chamber is sealed to the gas chamber with the delivery-side flexible barrier oriented directly adjacent to the gas-side flexible barrier. The delivery-side flexible barrier is pressed into the delivery chamber to dispense a delivery material from the delivery chamber in response to distension of the gas-side flexible barrier away from the gas-side rigid portion. The dispersion structure receives the delivery material from the chamber delivery pump. The dispersion structure delivers the delivery material to a delivery site. The control module is coupled to the gas cell. The control module controls an operating parameter of the gas cell. Other embodiments of the system are also described.

Certain embodiments include structure that is configured and arranged to resist spill of delivery material from the delivery device to the environment. For purpose of this disclosure, "spill" means undesired discharge of delivery material from the delivery chamber to the environment. Exemplary spill-resistant structure may include a passive gas-relief valve disposed in a venting association with the gas chamber to permit discharge of passive gas from inside the gas chamber to the environment. "Passive gas" is further defined below, but encompasses small non-operational amounts of gas evolved from a gas cell.

Operable spill-resistant structure may include an absorbent element disposed to facilitate completely filling the delivery chamber with delivery material during manufacture of a device. In certain cases, spill-resistant structure may encompass an overflow emanator chamber associated with the delivery aperture to receive and confine small quantities or even excessive drops of delivery material. Desirably, such an overflow emanator chamber is structured to hold a volume that is at least about half the volume held in a full delivery chamber. An absorbent element may sometimes be disposed inside the overflow emanator chamber to capture and confine discharged drops of delivery material while permitting emanation of volatized delivery material. A preferred absorbent element is made from a material that can soak up delivery material, and permit emanation of desirable volatile portions thereof. In certain cases, the absorbent element is also effective as an emanator, or is structured to communicate absorbed delivery material to an emanator.

In certain embodiments, a gas cell is self-powered. One self-powered gas cell operates under galvanic principles. Another operable gas cell may be powered by a remote or external source (e.g., by a battery), and is more properly characterized as an electrochemical cell. Regardless, it is preferred for a gas cell to be structured to resist generation of passive gas prior to the gas cell being placed into service to generate operational levels of gas.

There are various ways to structure a gas cell to resist undesired accumulation of passive gas in a gas chamber. Structure configured to avoid passive gas accumulation is regarded as encompassed within certain spill-resistant structure. It is within contemplation that a gas cell may be structured to permit on-demand release of fluid (e.g. water and/or electrolyte), from storage that is isolated from an electrode to place the cell into operational gas generating mode. Also, a gas cell may be structured to permit on-demand completion of an electrically conductive path disposed between an anode and a cathode of the gas cell to place the gas cell into operational gas generating mode. For example, a switch may be disposed to interrupt electrical continuity on a path between two electrodes. In other embodiments, a gas cell can be structured to permit on-demand coupling of on or more discrete components to place the cell into operational gas generating mode. Portions of a cell, or even the entire gas cell, may be stored at a nonoperational or remote position to avoid gas build-up in the gas chamber, and then placed into an operational position with respect to the gas chamber when operational gas generation is desired.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

In the drawings, which illustrate what are currently considered to be the best modes for carrying out the invention:

FIG. 1 depicts an exploded cut-away view in perspective of one embodiment of a delivery device;

FIG. 2 depicts a cut-away schematic diagram in perspective of one embodiment of the delivery device of FIG. 1 with the gas-side flexible barrier fully compressed;

FIG. 3 depicts a cut-away schematic diagram in perspective of one embodiment of the delivery device 100 of FIG. 1 with the delivery-side flexible barrier fully compressed;

FIG. 4 depicts a schematic diagram side view of one embodiment of the delivery device of FIG. 1 with the flexible barriers and in neutral position, and a gas generating cell in storage-stable configuration;

FIG. 5 depicts a schematic diagram side view of the embodiment in FIG. 4 with a gas generating cell in an operational configuration;

FIG. 6 depicts a schematic diagram side view of one embodiment of the delivery device of FIG. 1 with the flexible barriers and in neutral position, and a remote gas generating cell;

FIG. 7 depicts a block diagram of one embodiment of a method of manufacturing a multi-chamber delivery system;

FIG. 8 is a schematic view of gas generating cell operable for use in a fluid delivery system according to certain principles of the invention;

FIG. 9 is a schematic view of a gas generating cell operable for use in another workable fluid delivery system according to certain principles of the invention;

FIG. 10 is a cross-section side view of another workable fluid delivery system according to certain principles of the invention;

FIG. 11 is a schematic side view of another workable fluid delivery system according to certain principles of the invention; and FIG. 12 is an alternative embodiment of a pressurized chamber fragrance delivery system.

Throughout the description, similar reference numbers may be used to identify similar elements.

DETAILED DESCRIPTION OF THE ILLUSTRATED EMBODIMENT(S)

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments relate to a gas cell pump. Certain embodiments described below are drawn to delivery of a delivery material through mechanical pressure generated by a gas cell. Some embodiments may be useful to deliver medicines, scents, chemical agents, lubricants, saline, or other materials, chemicals, or chemical mixtures. In some embodiments, the pump may deliver the material to a local area. In other embodiments, the pump may deliver the material to a stream of material to yield a certain result at a near or relatively distant site. In another embodiment, the pump delivers the material at a sustained rate. For example, the pump may operate at a relatively slow rate of delivery or at a high rate. In other embodiments, the pump delivers the material at a variable rate.

In some embodiments, the pump can be loaded with a volatile and/or corrosive material for delivery. The pump can be built with materials that are specifically resistant to the particular chemical or agent that will be delivered by the pump. Additionally, some embodiments may incorporate materials that have a low permeability relative to the delivery agent. In this way, some embodiments may be specifically built to deliver a particular substance. Other embodiments may be built to handle a wide range of substances with varying corrosion and permeability characteristics.

In some embodiments, the components of the pump may be sealed together into a single unified piece. In other embodiments, some components may be joined in a manner that allows those components to be removed without damage to the pump or use of complex processes. For example, in some embodiments, the portion containing the delivery material may be removed to replace a spent portion with a new portion. In other embodiments, other portions may be removable.

In some embodiments, the pump is operable in any orientation. In other words, the pump is not sensitive to any particular orientation threshold. For example, the pump may be positioned to dispense a delivery material upwards, downwards, or at any angle in between.

FIG. 1 depicts an exploded cut-away view of one embodiment of a delivery device or pump 100. The illustrated embodiment includes a gas-side rigid portion 102, a gas-side flexible barrier 104, a delivery-side rigid portion 106, a delivery-side flexible barrier 108, a gas cell 110, and a delivery aperture 112. In the depicted embodiment, the gas-side rigid portion 102 is a domed geometry with a flanged edge. The structure of the gas-side rigid portion 102 corresponds with the structure of the gas-side flexible barrier 104. This allows the gas-side rigid portion 102 and the gas-side flexible barrier 104 to match up and form a seal. In other embodiments, the gas-side rigid portion 102 may have a different geometry than illustrated. For example, the gas-side rigid portion 102 may have a deeper curvature, it may be cylindrical or spherical, it may have planar portions or be cuboidal, and it may have a concave geometry rather than the convex geometry shown in FIG. 1.

In the pump embodiment 100 illustrated in FIG. 1, the gas-side rigid portion 102 has a smooth surface. In other embodiments, the gas-side rigid portion 102 has a surface treatment. For example, the surface treatment may include polishing, texturing, added structural elements to increase rigidity or provide some other functionality. In the depicted embodiment, the gas-side rigid portion 102 is made of a relatively rigid material. For example, the gas-side rigid portion 102 may be made of hard plastic, metal, composite, or some other rigid material.

In the embodiment 100 of FIG. 1, the gas-side flexible barrier 104 is coupled with the gas-side rigid portion 102. In some embodiments, the gas-side flexible barrier 104 is sealed to the gas-side rigid portion 102. For example, the gas-side flexible barrier 104 and the gas-side rigid portion 102 may be joined by thermal sealing, mechanical sealing, chemical sealing or adhesion, vacuum sealing, or a combination of several forms of sealing or creating a seal.

In some embodiments, the gas-side flexible barrier 104 is a flexible membrane that operates like a diaphragm. As the gas cell 110 generates gas, the gas-side flexible membrane 104 flexes to form a chamber between the gas-side flexible barrier 104 and the gas-side rigid portion 102. As the gas cell 110 continues to generate gas, the gas-side flexible barrier continues to flex to provide additional capacity within the chamber. In some embodiments, the material used for the gas-side flexible barrier 104 may be selected to have a high degree of resistance to reactivity with the gas generated by the gas cell 110. Additionally, the gas-side flexible barrier 104 may be selected to provide a low degree of permeability relative to the gas generated by the gas cell 110. In some embodiments, a material may be selected for both chemical reactivity and permeability. In other embodiments, additional qualities and characteristics may influence material selection for the gas-side flexible barrier 104. Materials which might be used either alone or in combination include acrylonitrile, methyl acrylate copolymer, poly ethylene terephthalate (PET), high density polyethylene (HDPE), also laminates such as biaxial aliphatic polyamides (also known as Nylon), aluminum foil, and low density polyethylene.

In some embodiments, the gas-side flexible barrier 104 is flexible throughout its entirety. In other embodiments, the gas-side flexible barrier 104 includes some rigid or relatively less-flexible portions incorporated within the gas-side flexible barrier 104. In some embodiments, the gas-side flexible barrier 104 has portions with varying degrees of flexibility. For example, the gas-side flexible barrier 104 may have a small rigid portion 111 that prevents the gas-side flexible barrier 104 from contacting the gas cell 110 when the gas-side flexible barrier 104 is fully collapsed against the gas-side rigid portion 102. Other embodiments incorporate other structural elements within the gas-side flexible barrier 104 to provide other functionality.

In some embodiments, the delivery-side rigid portion 106 is similar to the gas-side rigid portion 102. In other embodiments, the delivery-side rigid portion 106 is unique in form and functionality. For example, the delivery-side rigid portion 106 may be formed to improve the flow of delivery material to the delivery aperture 112 or may include a refill interface (not shown). Other functionality and structure may be included in other embodiments. In some embodiments, the delivery-side rigid portion 106 matches the form of the gas-side rigid portion 102 where they meet to facilitate sealing the delivery side (e.g., 116 of FIG. 4) and the gas side (e.g., 114 of FIG. 4) together. In other embodiments, the delivery-side rigid portion 106 varies in geometry from the gas-side rigid portion 102.

In the embodiment 100 depicted in FIG. 1, the delivery-side flexible barrier 108 is coupled to the delivery-side rigid portion 106. In some embodiments, the delivery-side flexible barrier 108 is formed of material with a high degree of chemical resistance relative to a delivery material. In other embodiments, the delivery-side flexible barrier 108 also has a low degree of permeability relative to the delivery material. In some embodiments, the delivery-side flexible barrier 108 has a high degree of permeability relative to the gas generated by the gas cell 110. This would allow any stray gas from the gas cell 110 that has collected on the delivery side 116 to escape through the delivery-side flexible barrier 108 without forming a bubble or otherwise affecting the delivery side 116 of the device 100. In some embodiments, similar gas venting functionality is incorporated into the delivery-side rigid portion 106.

In the device illustrated in FIG. 1, the gas cell 110 is disposed in the structure of the gas-side rigid portion 102. In some embodiments, the gas cell 110 is disposed in the structure of the gas-side rigid portion 102 by application of a glass bead, silicon bead, cyanoacrylate adhesive or other form of sealant or adhesive material or process. In some embodiments, the gas cell 110 may be located at a remote site and be connected by channels or tubes to direct the gas generated by the gas cell 110 through the gas-side rigid portion 102. The gas cell 110 produces a gas and directs the gas into the area between the gas-side rigid portion 102 and the gas-side flexible barrier 104. The buildup of the gas in this area forces the gas-side flexible barrier 104 to move away from the gas-side rigid portion 102. This provides the driving forces for operation of the device.

In some delivery devices or pumps 100, the gas cell 110 is an electrochemical cell. Gas cell technology is taught by Gordon in U.S. Pat. Nos. 5,744,014 and 5,899,381 which are incorporated herein by reference The embodiment 100 illustrated in FIG. 1 includes a delivery aperture 112. In some embodiments, the delivery aperture 112 is a separate structure disposed in the delivery-side rigid portion 106. In other embodiments, the delivery aperture 112 is formed as part of the delivery-side rigid portion 106. The delivery aperture 112 allows a delivery material to be released from the delivery side 116 of the device 100. In some embodiments, a delivery aperture 112 may include a valve (e.g., 117 in FIG. 10) to prevent release of the delivery material until a certain pressure threshold or other criteria are reached. In some embodiments, the delivery aperture 112 includes an attachment point to facilitate attachment of a dispersion structure (discussed further below) to disperse the delivery material released through the delivery aperture 112. In some embodiments, the delivery aperture 112 is made of or includes an activator to cause a chemical reaction in the delivery material as it passes through the delivery aperture 112. For example, the delivery aperture 112 may include a heater, a chemical activator, an electrically charged element, or other structure to interact with the delivery material as it passes through the delivery aperture 112. In another embodiment, the delivery aperture 112 physically affects the delivery mode of the delivery material. For example, the delivery aperture 112 may atomize, collimate, stream, spread, accelerate, slow, vary, or modulate the delivery of the delivery material.

Although the delivery device 100 is shown and described with certain components and functionality, other embodiments of the delivery device 100 may include fewer or more components to implement less or more functionality.

Figure 2:
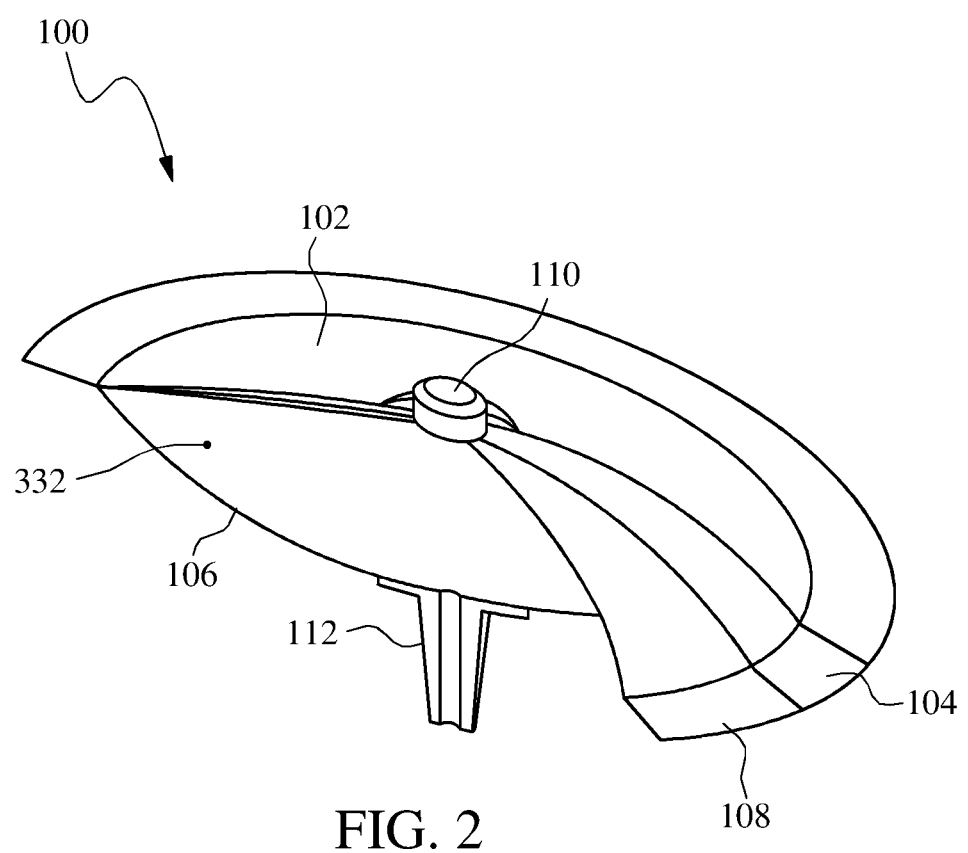

FIG. 2 depicts a cut-away schematic diagram of one embodiment of a delivery device 100 of FIG. 1 with the gas-side flexible barrier 104 fully compressed. The illustrated embodiment of the delivery device 100 includes the gas-side rigid portion 102, the gas-side flexible barrier 104, the delivery-side rigid portion 106, the delivery-side flexible barrier 108, the gas cell 110, and the delivery aperture 112.

As illustrated in FIG. 2, the delivery side (116, see FIG. 4) has been loaded with a delivery material so that the delivery-side flexible barrier is extended. This compresses the gas side (114, FIG. 4) so that the gas-side flexible barrier 104 conforms to the form of the gas-side rigid portion 102. Still with reference to FIG. 2, the gas cell 110 has not begun generating gas and the gas-side flexible barrier 104 is collapsed against the gas-side rigid portion 102. Once the gas cell 110 begins generating gas, the area between the gas-side rigid portion 102 and the gas-side flexible barrier 104 will fill with the gas and the gas-side flexible barrier 104 will begin to compress the delivery-side flexible barrier 108. This will result in increased pressure between the delivery-side flexible barrier 108 and the delivery-side rigid portion 106.

Figure 3:
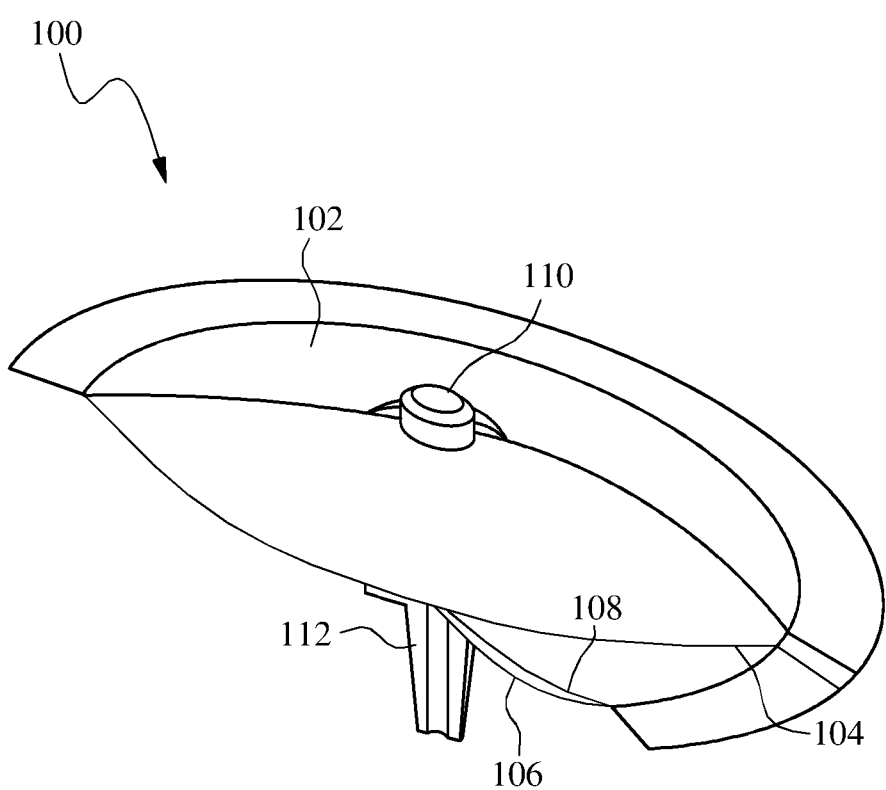

FIG. 3 depicts a cut-away schematic diagram of one embodiment of the delivery device 100 of FIG. 1 with the delivery-side flexible barrier 108 fully compressed. In the illustrated embodiment, the gas cell 110 has generated enough gas to force the gas-side flexible barrier 104 away from the gas-side rigid portion 102 to compress the delivery-side flexible barrier 108. This has expelled the delivery material through the delivery aperture 112 and collapsed the delivery-side flexible barrier 108 against the delivery-side rigid portion 106.

Figure 4:
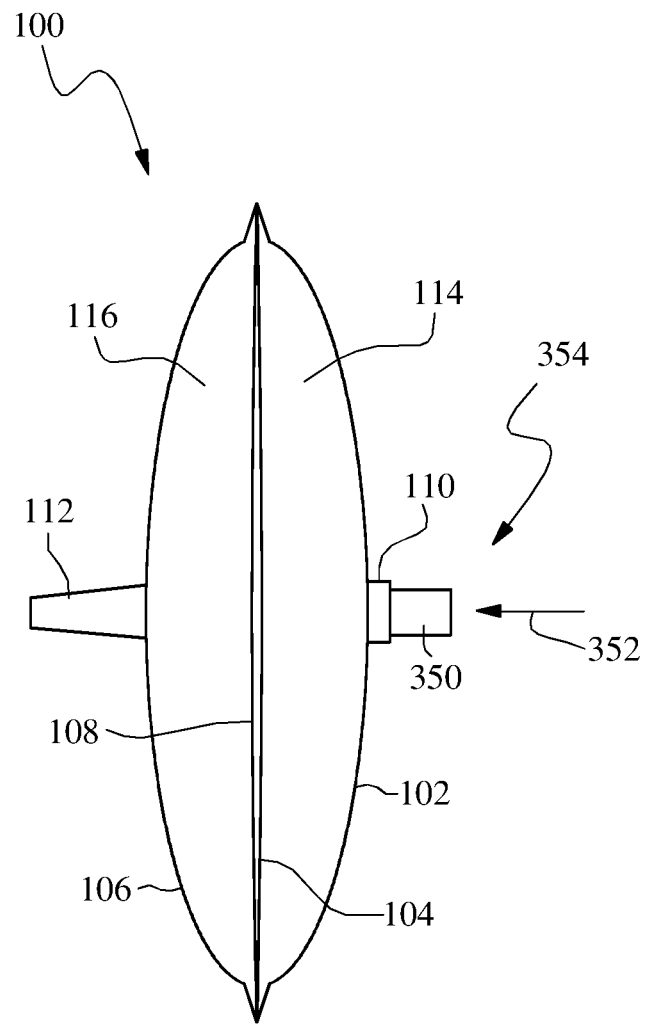

FIG. 4 depicts a schematic diagram of one embodiment of the delivery device 100 of FIG. 1 with the flexible barriers 104 and 108 in neutral position. In the illustrated embodiment, the gas-side flexible barrier 104 and the delivery-side flexible barrier 108 are in neutral position. This more readily depicts the gas chamber 114 or gas side 114 of the delivery device 100 as well as the delivery chamber 116 or delivery side 116 of the delivery device 100. In the illustrated embodiment of FIG. 4, the gas-side flexible barrier 104 and the delivery-side flexible barrier 108 are separated by a small margin. In some embodiments, the relatively small space between the gas-side flexible barrier 104 and the delivery-side flexible barrier 108 is filled with a buffer material to reduce friction and binding between the gas-side flexible barrier 104 and the delivery-side flexible barrier 108. In other embodiments, the gas-side flexible barrier 104 and the delivery-side flexible barrier 108 are in direct contact without separation. In some embodiments, one or both of the gas-side flexible barrier 104 and the delivery-side flexible barrier 108 include surface treatments to reduce friction and substantially prevent binding between the gas-side flexible barrier 104 and the delivery-side flexible barrier 108.

Figure 6:
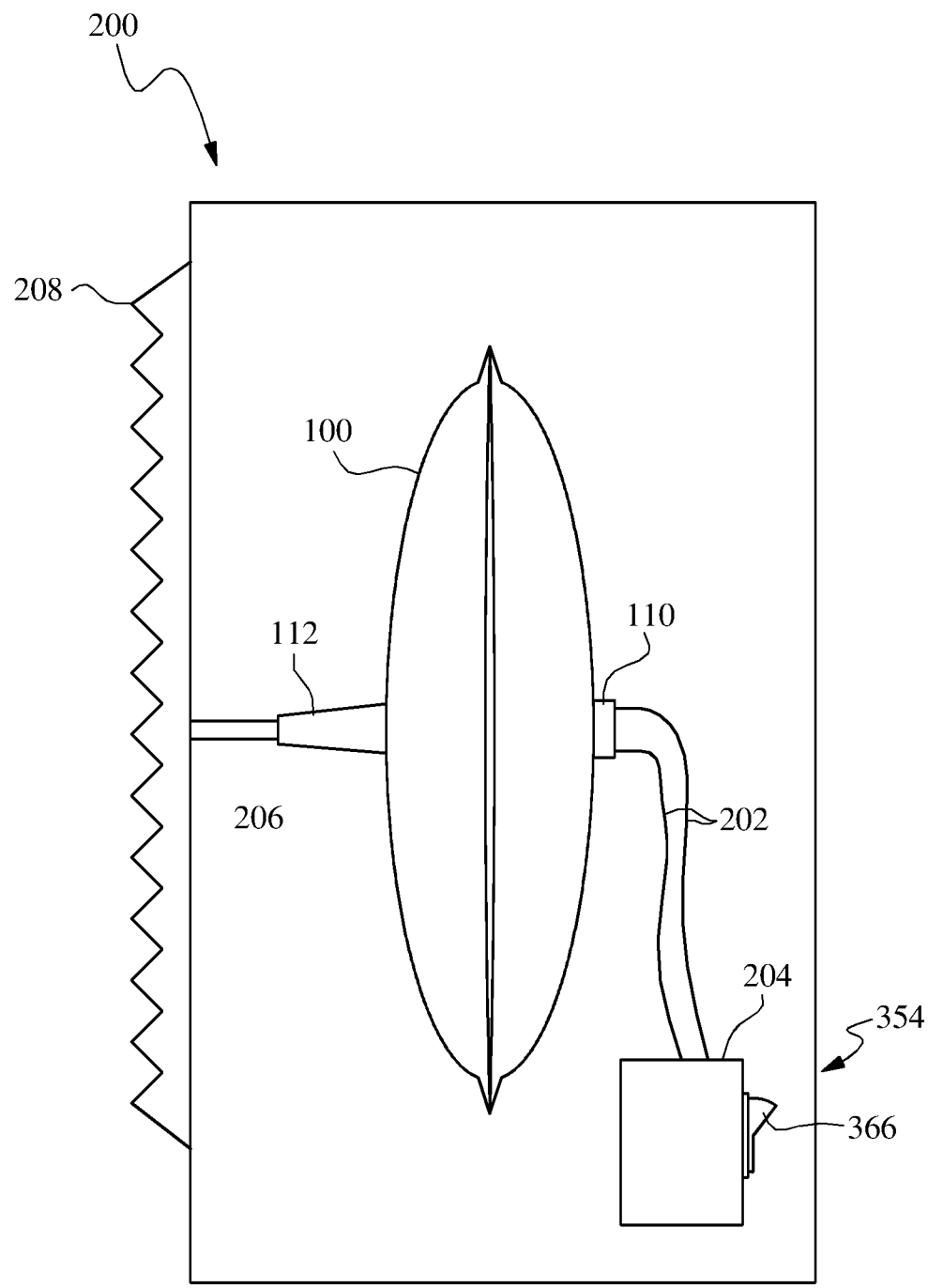

FIG. 6 depicts a schematic diagram side view of one embodiment of a delivery system 200. The illustrated embodiment 200 includes a delivery pump 100, a control module 204, leads 202, delivery line 206, and dispersion structure 208. In the illustrated embodiment, the pump 100 includes a gas cell 110 and a delivery aperture 112. In the illustrated embodiment, the pump 100 is in a vertical orientation. In other embodiments, the pump may be oriented horizontally, or at some other angle. In the illustrated embodiment, the gas cell 110 is connected by leads 202 to a control module 204. In some embodiments, the control module 204 includes resistive elements to control the gas cell 110. Other embodiments include other types of electrical or mechanical control systems.

In the illustrated embodiment 200, the delivery aperture 112 is connected to the delivery line 206. In some embodiments, the delivery line 206 is a tube or channel. The delivery line 206 is connected to the dispersion structure 208 to communicate a delivery material from the delivery aperture 112 of the pump 100 to the dispersion structure 208. In some embodiments, the delivery line 206 is omitted and the delivery aperture 112 is in direct communication with the dispersion structure 208. In some embodiments, the dispersion structure 208 is a molecular dispersion media. For example, the dispersion structure 208 may include gauze, foam, sponge, or other breathable surface area. In another embodiment, the dispersion structure 208 is a spray nozzle. In other embodiments, the dispersion structure 208 is a tube, a needle, a heated element, or other known mechanical, thermal, chemical or other element for delivery of a material to a target location or environment. In another embodiment, the dispersion structure 208 is omitted and the delivery aperture 112 disperses the delivery material from the pump directly out from the delivery system 200. In some embodiments, the pump 100 is implemented within the delivery system 200 to provide certain advantages over conventional technologies. For example, some embodiments of the delivery system 200 implement the pump 100 to eliminate orientation dependencies. For example, the delivery system 200 may be oriented in any direction without suffering leakage or failure in the pump 100. Other embodiments of the delivery system 200 may implement the pump 100 to achieve other advantages.

Although the delivery system 200 is shown and described with certain components and functionality, other embodiments of the delivery system 200 may include fewer or more components to implement less or more functionality.

Figure 7:
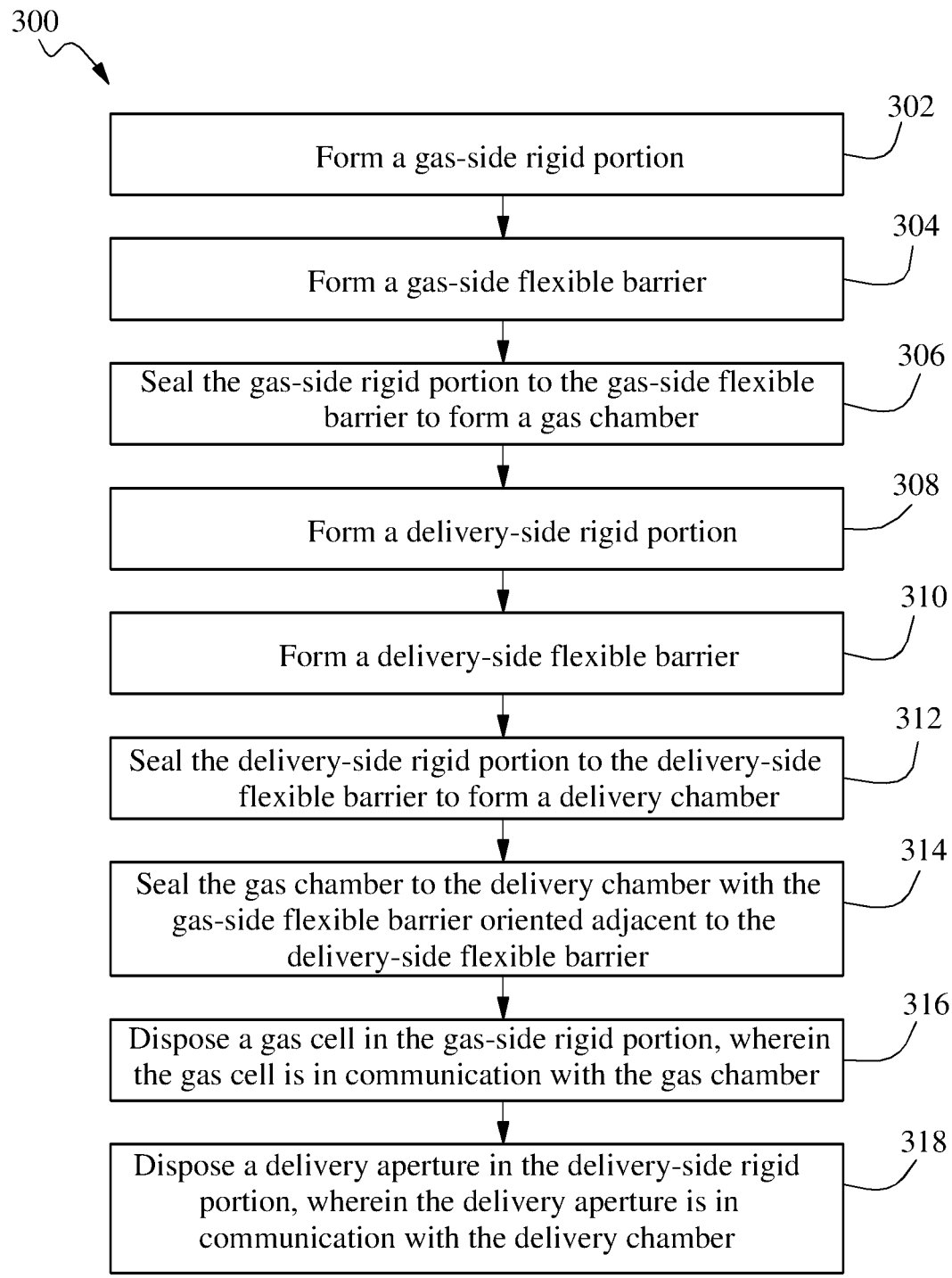

FIG. 7 depicts a block diagram of one embodiment of a method 300 of manufacturing a chamber delivery system. At block 302, a gas-side rigid portion is formed. At block 304, a gas-side flexible barrier is formed. At block 306, the gas-side rigid portion is sealed to the gas-side flexible barrier to form a gas chamber. At block 308, a delivery-side rigid portion is formed. At block 310, a delivery-side flexible barrier is formed. At block 312, the delivery-side rigid portion is sealed to the delivery-side flexible barrier to form a delivery chamber. At block 314, the gas chamber is sealed to the delivery chamber with the gas-side flexible barrier oriented adjacent to the delivery-side flexible barrier. At block 316, a gas cell is disposed in the gas-side rigid portion. The gas cell is in communication with the gas chamber. At block 318, a delivery aperture is disposed in the delivery-side rigid portion. The delivery aperture is in communication with the delivery chamber.

It is desirable to provide structure or to otherwise craft a device 100 to resist spill of delivery material from the device 100. Gas that is present in the delivery chamber 116 and that undergoes a temperature increase may cause a much larger undesired discharge of delivery material than expansion of the storage material, itself, due to the same temperature increase. Therefore, it is desirable to minimize gas entrapped inside the storage chamber 116. With reference again to FIG. 1, it is within contemplation to include an absorbent element 330, such as a sponge, to facilitate completely filling the storage volume 332 of a delivery chamber 116 with delivery material during manufacture of a device 100. In that case, entrapment of air bubbles in the storage/delivery chamber 116 when charging the chamber 116 with a delivery material is significantly reduced, or desirably, eliminated. The resulting device 100 is more resistant to spilling or undesirably discharging delivery material 334 due to an increase in temperature of the storage or service environment. A preferred absorbent element 330 is configured to virtually or completely fill the volume of a fully charged delivery chamber 116 when saturated or loaded with the delivery material.

Sometimes, a gas generating cell 110 may generate a spurious small amount of gas during storage or other non-operating periods. For purpose of this disclosure, such spurious gas is characterized as passive gas, or non-operating gas. Non-operating gas generation may occur at a Zinc electrode when that electrode is bathed in an electrolyte, due to impurities that are realistically inherent in that electrode, for one example. Also, an electrolyte may contain a certain amount of reactive ions that react at an electrode to generate gas until a protective surface film is developed on the electrode, for a second non-limiting example. Therefore, as an alternative or additional measure to reduce spilling or undesired discharge of delivery material from confinement in the delivery chamber 116 to the environment, a passive gas-relief valve 336 may be included in a venting association with a gas chamber 114. As illustrated in FIG. 1, a workable passive gas-relief valve 336 may be structured as a gas-permeable membrane disposed to cover a window through gas-side rigid portion 102. A gas-relief valve 336 is operable to permit a certain small amount of gas (e.g., passive gas) to slowly migrate from chamber 114 through the valve 336 to the environment to avoid pressure build-up inside the gas chamber 114. Therefore, the small quantities of gas, which may be slowly generated by a gas generating cell 110 during non-operational storage of a device 100, will not accumulate and create a discharge pressure to cause a spill of delivery material. However, a workable gas-relief valve 336 does not permit gas discharge from chamber 114 at a rate sufficient to reduce operational capability of the device 100 once the gas generating cell 110 is placed into an operation mode to generate gas for conventional use of device 100.

As another option to reduce or avoid spills of delivery material, an overflow emanator chamber 338 may be associated with a delivery aperture 112 to receive small quantities or even excessive drops of delivery material 334. Desirably, an overflow emanator chamber 338 is structured to confine a volume 340 that is at least about half the volume of delivery material that is initially confined in delivery chamber 116. As another option, it is within contemplation to further include an absorbent element 342 disposed inside the volume 340. In the latter case, undesirably discharged drops of delivery material 334 may be captured and confined to resist spilling delivery material from the device 100. A workable absorbent element 342 may be a sponge, or other such material that can soak up delivery material, and permit emanation of desirable volatile portions thereof. Desirably, absorbent element 342 is also effective as an emanator, or serves to communicate absorbed delivery material to an emanator.

Figure 5:
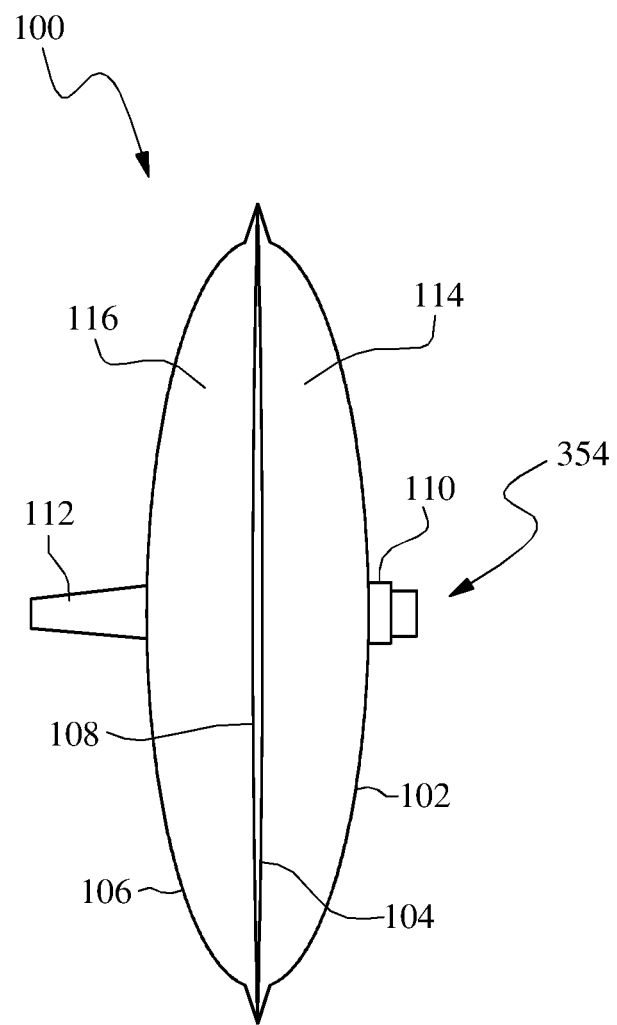

It is within contemplation that a gas generating valve 110 may be structured to resist generation of gas prior to placing the valve 110 into operation to dispense delivery material. With reference to FIGS. 4 and 5, a gas-generating valve 110 may be structured for storage in a configuration that decouples at least one reactive element from operational contact with another element. In FIG. 4, the valve 110 is illustrated in a decupled configuration. Displacement of element 350 in an actuating direction (such as transverse direction 352) to couple elements or otherwise permit operation of valve 110 is effective to enable the gas-generating valve 110 to produce gas, as illustrated in FIG. 5. An actuation direction may be embodied to include one or more of a displacement and a rotation.

Operable de-coupling structure, generally indicated at 354, may be configured, as non-limiting examples, to interrupt an electric path between electrodes, or to isolate an electrolyte from operational contact with electrodes. A portion of a gas-generating cell 110 may even be provided as an element that is physically separate from the bulk of a device 100, and the distinct elements can be coupled together in an operational configuration to generate operational quantities of gas at the time the device 100 is placed into service to dispense delivery material. In the latter case, decoupling structure encompasses distance and physical separation between constituent elements. Discrete elements within contemplation include individual active elements, such as electrolyte, or a portion of a conductive path extending between electrodes of the cell. The gas generating cell, itself, can even be stored as a discrete component and assembled in operational registration with a gas chamber at the time when a device 100 is placed into service.

Figure 8:
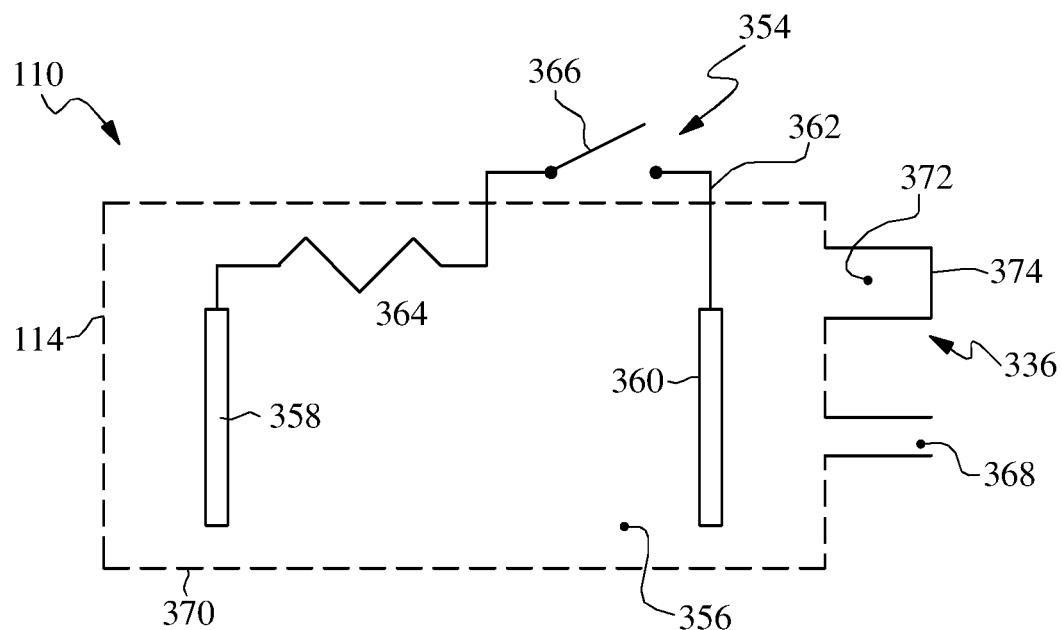

FIG. 8 illustrates a self-powered galvanic gas cell 100 that is structured to resist an internal build-up of passive gas. The gas chamber 114 holds an electrolyte 356 in operable association with a Zinc anode 358 and carbon cathode 360. A workable electrolyte includes KOH and $H_2O$. An interruptible electrically conductive path 362 (e.g., a metal wire) is provided between the anode and cathode. Hydrogen gas $H_2$ is evolved at the Zinc anode 358, according to the overall reaction $Zn+H_2O=>ZnO+H_2$, and the rate of gas production can be controlled by the value of the resistor 364. A workable resistor may have a resistance between about 1000 and about 8000 ohms. It is preferred to include decoupling structure 354, such as switch 366 to place the cell 110 in either an operational condition, or a non-operational condition, as desired. Evolved operational gas may be ported through exit 368 to a different remote gas chamber (not illustrated), or a wall 370 of chamber 114 may be embodied as a flexible membrane to engage a cooperating membrane of a proximal delivery chamber 116. An optional passive gas-relief valve 336 may be included. Illustrated gas-relief valve 336 includes a window 372 through a wall of the chamber 114, and a gas permeable membrane 374 to allow escape of passive gas, while resisting undue escape of operational gas.

Figure 9:
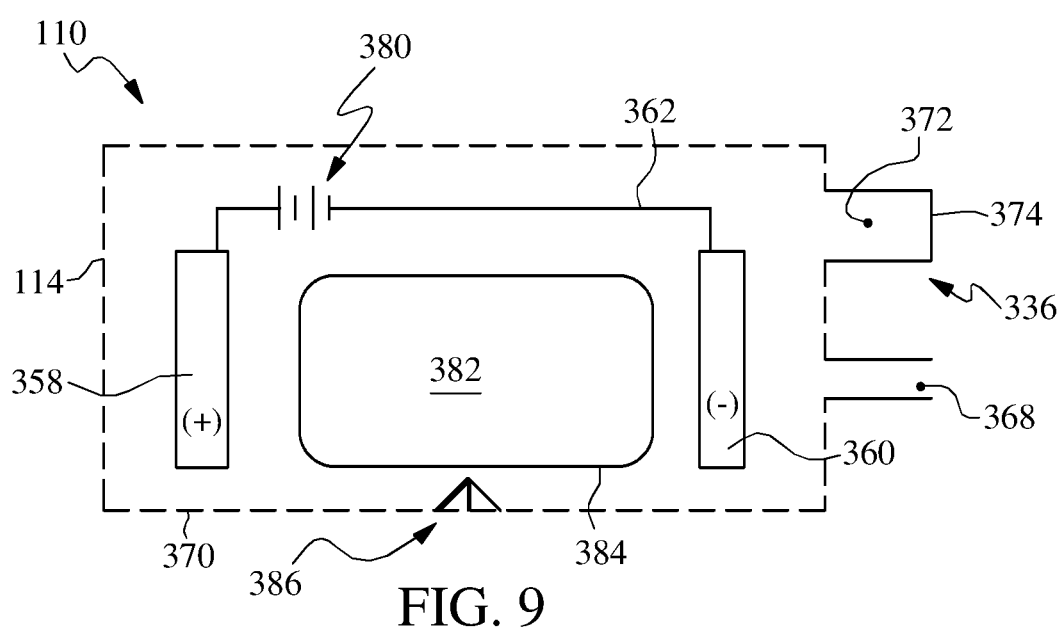

FIG. 9 illustrates an electrochemical gas generating cell 110 that is also structured to resist an internal build-up of passive gas. Certain elements are similar to like elements in FIG. 8, and are numbered accordingly. An external power source, generally 380, is operably connected to anode 358 and cathode 360 by way of conductor 362. Initially, a quantity of electrolyte 382 is confined inside membrane pouch 384, and is therefore prevented from reacting with the anode and cathode. As illustrated, a puncture device, generally 386, may be arranged to puncture the membrane 384 and thereby permit electrolyte 382 to react with the anode and cathode under influence of, and generate a gas when the cell 110 is placed into operational mode.

Figure 10:
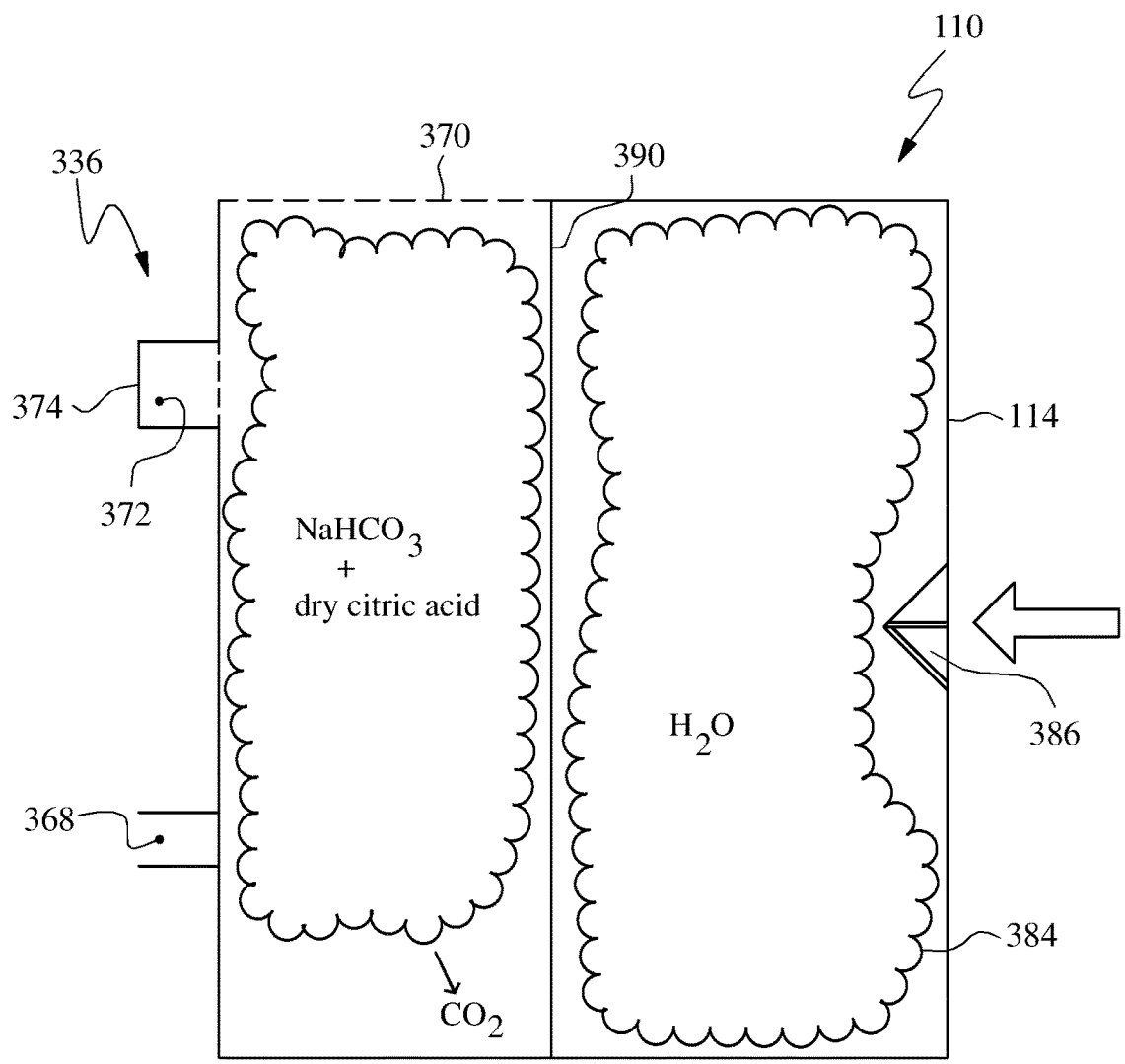

FIG. 10 illustrates another gas cell 110 that is structured to resist build-up of passive gas during storage of a delivery device 100. Again, certain elements are similar to like elements in FIGS. 8 and 9, and are numbered accordingly. A quantity of sodium carbonate and anhydrous citric acid are disposed on one side of a moisture-permeable membrane 390 inside gas chamber 114. A fluid, such as water ($H_2O$) is disposed on the other side of membrane 390, and is initially confined in a membrane pouch 384. When the gas cell is to be used to generate gas, puncture device 386 may be used to release the fluid from confinement. In the case where the fluid is water, the water can pass through the membrane 390 to react with the sodium carbonate and anhydrous citric acid. The reaction rate and corresponding evolution of gas ($CO_2$) will be at a rate controlled by permeation properties of the membrane 390. Passive gas is not evolved in the embodiment illustrated in FIG. 10, because dry sodium carbonate and anhydrous citric acid do not react without the presence of fluid. However, a passive gas relief valve 336 may be included to accommodate a pressure change during storage, where the pressure change corresponds to temperature change in air unavoidably present in chamber 114.

Figure 11:
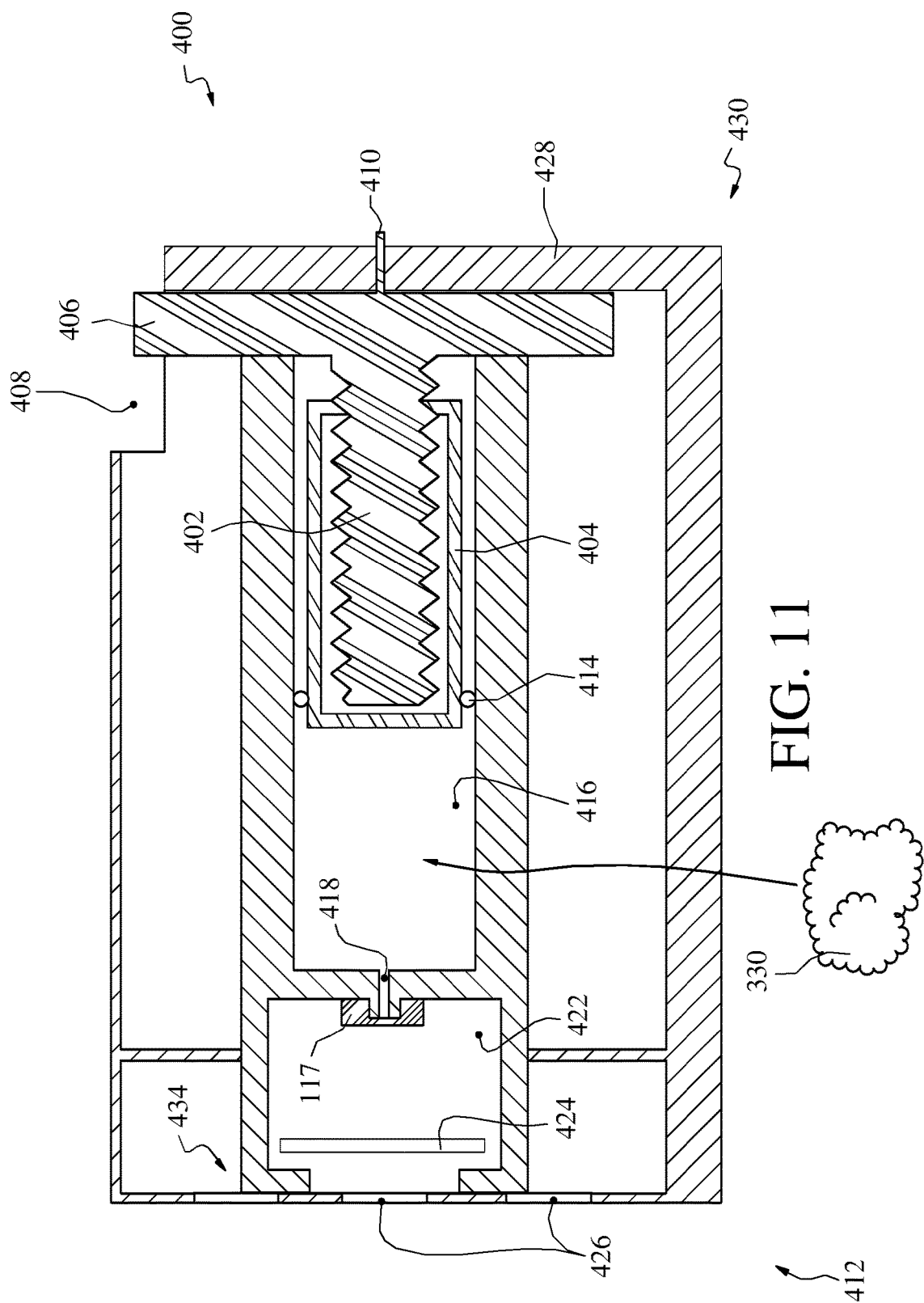

FIG. 11 illustrates another embodiment of a manual fragrance delivery system 400 which includes a threaded actuator shaft 402 that is rotated by way of a user interacting with actuator knob 406. Threaded shaft 402 engages a threaded wall at the proximal end of the piston plunger 404. Window 408 provides access for a user's finger to engage actuator knob 406. Knob 406 may be rotated about axle 410 to cause a compression in the shaft 402 and drive piston plunger 404 toward the discharge end, generally indicated at 412. Piston plunger 404 is sealed on its distal end, as indicated at O-ring 414, to urge volatile fluid contained inside plunger chamber 416 (AKA volatile fluid or delivery material chamber 116) toward aperture 418 for discharge into the local environment.

Certain embodiments may include a valve member 117 to resist unintended discharge of fluid. One operable valve member 117 establishes a threshold pressure required before fluid is permitted to flow through the discharge aperture 418.

Further, a safety emanator chamber 422 may be provided to hold a quantity of fluid that is improperly, or accidentally, discharged. For example, a child may play with the discharge mechanism 406 and discharge a significant portion of fluid. Safety reservoir 422 provides a catch basin to hold the fluid, rather than permit the fluid to leak onto and damage e.g., upholstery or carpeting in an automobile. A safety reservoir 422 within contemplation may be sized to hold the entire initial (or as-manufactured) contents of volatile fluid chamber 416. Preferably, emanator chamber 422 is sized to accommodate at least half the volume that is confined in chamber 416 at time of manufacture. An emanator 424 is typically provided to facilitate distribution and evaporation of the volatile fluid in chamber 422 over a larger area. Evaporated volatile fluid is then dispensed to the local environment through one or more apertures 426.

It is preferred for threaded shaft 402 to be left-hand threaded. As indicated above, the threaded shaft 402 is placed into compression to urge motion of plunger 404. The proximal end portion 428 of housing 430 forms a fixed restraint against which the actuator knob 406 presses to urge motion of the plunger 404. The window 408 is formed in housing 430, and permits a user access to manipulate actuator knob 406. Foot 434 is engaged on discharge end 412, so as plunger 404 moves distally, a volume in chamber 416 can be reduced to discharge volatile fluid from the chamber 416. As is the case with certain other embodiments, sometimes an absorbent element 330 may be included in the delivery chamber 416 to facilitate removal of gasses from the chamber 416 during manufacture of a device 400. The absorbent element 330 collapses, as the volume of chamber 416 is reduced by displacement of plunger 404, to release volatile fluid for discharge through aperture 418 toward a local ambient environment. It is further within contemplation that an absorbent element 330 may also, or alternatively, be disposed inside safety emanator reservoir 422, similar to a previously described embodiment.

Figure 12:
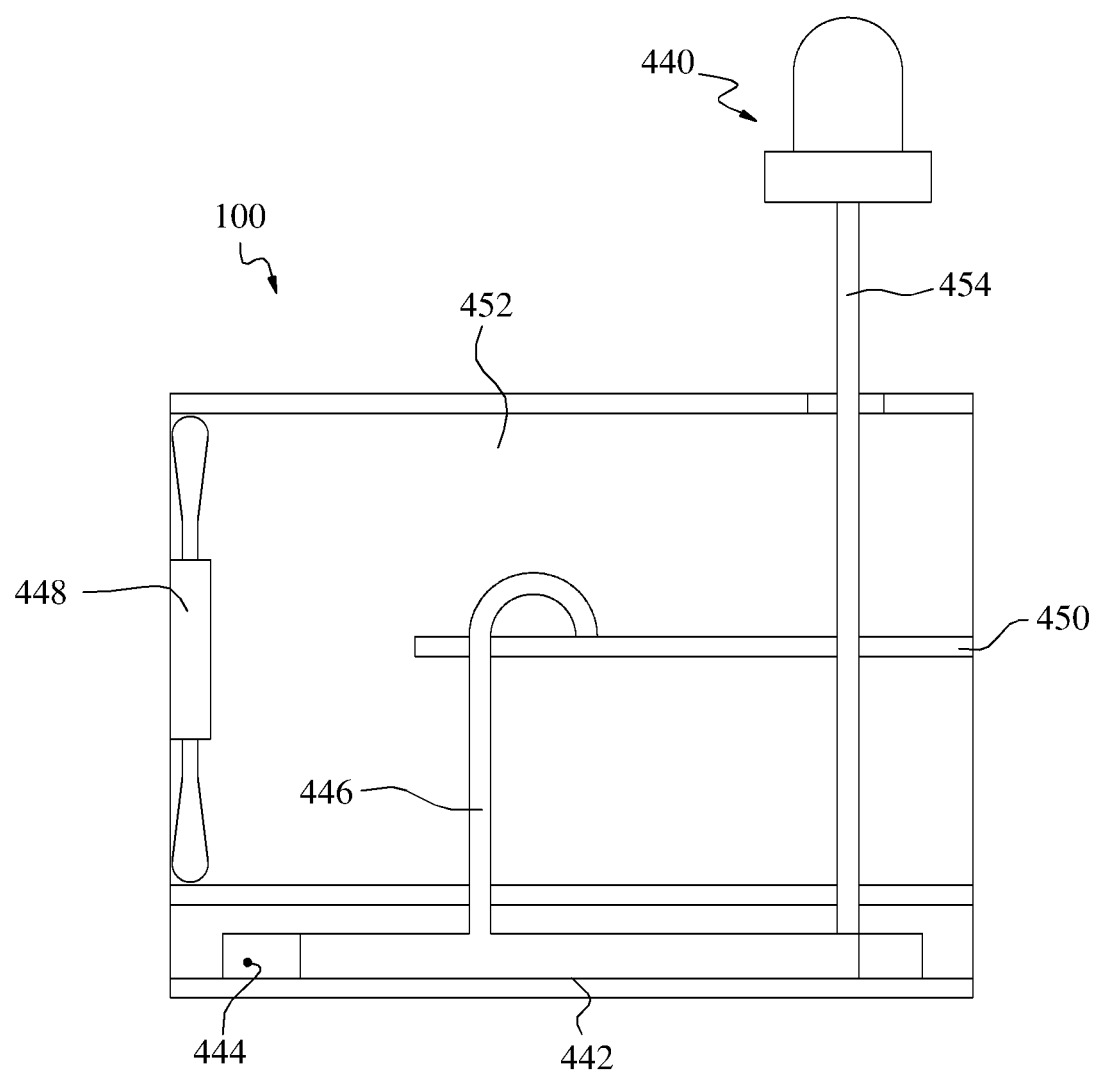

FIG. 12 illustrates an alternative embodiment of a pressurized chamber fragrance delivery system 100 configured to impart fragrance to a local environment. The illustrated pressurized chamber fragrance delivery system 100 includes a manual pump 440, a fragrance bag 442, an air chamber 452, a fragrance exit channel 446, a fan 448, an emanator 450, an air channel 452, and an air tube 454. Although the illustrated pressurized chamber fragrance delivery system 100 includes certain components to achieve specific functionality, other embodiments of the pressurized chamber fragrance delivery system 100 may include fewer or more components to achieve similar or different functionality.

In one embodiment, the manual pump 440 is used to pressurize the air chamber 444 containing the flexible fragrance bag 442. In one embodiment, the manual pump 440 is a manual air pump. Other embodiments may use other types of pumps. Pressurizing the air chamber 444 compresses the fragrance bag 442 to expel fragrance from the fragrance bag 442 through the fragrance exit channel 446 to the emanator 450. Some examples of emanator materials include, but are not limited to, porous polymers, simple cellular papers or films. In general, embodiments of the emanator 450 have a balance of absorption, wicking, and emanation properties that allow the emanator 450 to collect, distribute, and release the fragrance over time. The fan 448 moves air over the emanator 450 to deliver the fragrance into the ambient environment.

In some embodiments, the emanator 450 includes a porous material to collect, wick, and release the fragrance. The emanator 450 may or may not have its own structural integrity to maintain a specific shape while mounted within the fragrance delivery system. In some embodiments, the emanator material is applied to, or supported by, another support structure such as a cage or frame made of any suitable material.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An orientation independent delivery device comprising:
a gas chamber comprising a gas-side rigid portion and a gas-side flexible barrier element, wherein the gas-side flexible barrier element is permanently sealed, around a first perimeter of the gas chamber, to the gas-side rigid portion such that gas introduced to the gas chamber is confined between the gas-side flexible barrier element and the gas-side rigid portion;
a delivery chamber comprising a delivery-side rigid portion and a delivery-side flexible barrier element, wherein the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion, the delivery-side flexible barrier element being oriented adjacent to, and a distinct element from, the gas-side flexible barrier element;
an absorbent element disposed in the delivery chamber to avoid presence of air bubbles and facilitate completely filling the delivery chamber with delivery material during manufacture of said delivery device;
a gas cell coupled to the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element;
a delivery aperture to allow a delivery material to escape from the delivery chamber in response to deflection of the delivery-side flexible barrier element in a direction toward the delivery-side rigid portion to reduce a volume defined inside the delivery chamber; and
a capture element coupled to the delivery device and disposed downstream of the delivery aperture to resist spill of unintentionally discharged delivery material from the delivery chamber to the environment as a result of an undesired reduction in the volume or due to a temperature change-induced increase in pressure inside the delivery chamber, the capture element permitting release into the local atmosphere of delivery material in vapor form and resisting discharge of delivery material in liquid form, wherein:
the gas-side flexible barrier element has an outer surface that is in continuous direct contact with the delivery-side flexible barrier element without separation.

2. The delivery device according to claim 1, further comprising:
a passive gas-relief valve disposed in a venting association with the gas chamber to permit discharge of passive gas from inside the gas chamber to the environment.

3. The delivery device according to claim 1, wherein the capture element comprises:
an overflow emanator chamber associated with the delivery aperture to receive and confine small quantities or even excessive drops of delivery material.

4. The delivery device according to claim 3, wherein:
the overflow emanator chamber is structured to hold a volume that is at least half the volume held in a full delivery chamber.

5. The delivery device according to claim 3, further comprising:
an absorbent element disposed inside the overflow emanator chamber to capture and confine discharged drops of delivery material while permitting emanation of volatized delivery material.

6. The delivery device according to claim 5, wherein:
the absorbent element is made from a material that can soak up delivery material, and permit emanation of desirable volatile portions thereof.

7. The delivery device according to claim 5, wherein:
the absorbent element is also an emanator, or is structured to communicate absorbed delivery material to an emanator.

8. The delivery device according to claim 1, wherein:
the gas cell is self-powered.

9. The delivery device according to claim 8, wherein:
the gas cell is a galvanic cell.

10. The delivery device according to claim 1, wherein:
the gas cell is structured to resist generation of passive gas prior to the gas cell being placed into service to generate operational levels of gas.

11. The delivery device according to claim 10, wherein:
the gas cell is structured to permit on-demand release of electrolyte from storage that is isolated from an electrode to place the cell into operational gas generating mode.

12. The delivery device according to claim 10, wherein:
the gas cell is structured to permit on-demand completion of an electrically conductive path disposed between an anode and a cathode of the gas cell to place the gas cell into operational gas generating mode.

13. The delivery device according to claim 10, wherein:
the gas cell is structured to permit on-demand coupling of discrete components to place the cell into operational gas generating mode.

14. An orientation independent delivery device comprising:
a gas chamber comprising a gas-side rigid portion and a gas-side flexible barrier element, wherein the gas-side flexible barrier element is permanently sealed, around a first perimeter of the gas chamber, to the gas-side rigid portion such that gas introduced to the gas chamber is confined between the gas-side flexible barrier element and the gas-side rigid portion;
a delivery chamber comprising a delivery-side rigid portion and a delivery-side flexible barrier element, wherein the delivery-side flexible barrier element is permanently sealed, around a second perimeter of the delivery chamber, to the delivery-side rigid portion such that delivery material introduced to the delivery chamber is confined between the delivery-side flexible barrier element and the delivery-side rigid portion, the delivery-side flexible barrier element being oriented adjacent to, and a distinct element from, the gas-side flexible barrier element;
an absorbent element disposed inside the delivery chamber upon assembly of the device to facilitate complete filling of the delivery chamber with delivery material without entrapping air bubbles in the delivery chamber
a self-powered gas cell coupled to the gas-side rigid portion of the gas chamber, the gas cell to increase a gas pressure within the gas chamber to expand the gas-side flexible barrier element, wherein expansion of the gas-side flexible barrier element applies a compressive force to the delivery-side flexible barrier element;
a delivery aperture to allow a delivery material to escape from the delivery chamber in response to deflection of the delivery-side flexible barrier element in a direction toward the delivery-side rigid portion; and
means to resist spill of unintentionally discharged liquid delivery material from the delivery device to a local environment, the means to resist spill being coupled to the delivery device and disposed downstream of the delivery aperture, wherein:
the gas-side flexible barrier element has an outer surface that is in continuous direct contact with the delivery-side flexible barrier element without separation.

15. The delivery device according to claim 14, wherein:
the self-powered gas cell is a galvanic cell.

16. The delivery device according to claim 14, wherein:
the self-powered gas cell is structured for final assembly by a user to permit placing the gas cell into operational gas generating mode at the time of placing the delivery device into service to deliver material to the environment.

17. The delivery device according to claim 14, further comprising:
a passive relief valve disposed in a venting association with the gas chamber to permit discharge of passive gas from inside the gas chamber to the environment.

18. The delivery device according to claim 14, wherein:
the means to resist spill comprises an overflow emanator storage chamber associated with the delivery aperture to receive and confine spilled drops of delivery material, the overflow emanator storage chamber comprising a volume at least half as large as the delivery chamber volume.

* * * * *